(12) United States Patent
Lim et al.

(10) Patent No.: US 7,938,856 B2
(45) Date of Patent: May 10, 2011

(54) HEART VALVE ANNULOPLASTY PROSTHESIS SEWING CUFFS AND METHODS OF MAKING SAME

(75) Inventors: Jyue Boon Lim, Minneapolis, MN (US); Andrea L McCarthy, Vadnais Heights, MN (US)

(73) Assignee: St. Jude Medical, Inc., St. Paul, MN (US)

( * ) Notice: Subject to any disclaimer, the term of this patent is extended or adjusted under 35 U.S.C. 154(b) by 368 days.

(21) Appl. No.: 11/126,432

(22) Filed: May 10, 2005

(65) Prior Publication Data

US 2005/0256567 A1    Nov. 17, 2005

Related U.S. Application Data

(60) Provisional application No. 60/571,437, filed on May 14, 2004.

(51) Int. Cl.
 *A61F 2/24* (2006.01)
(52) U.S. Cl. .................................................... 623/2.36
(58) Field of Classification Search ................. 623/2.36, 623/2.38, 2.41, 2.37, 2.39, 2.4, 901
See application file for complete search history.

(56) References Cited

U.S. PATENT DOCUMENTS

| | | | |
|---|---|---|---|
| 3,142,067 A * | 7/1964 | Liebig | 623/1.51 |
| 3,656,185 A | 4/1972 | Carpentier | |
| 3,714,671 A * | 2/1973 | Edwards et al. | 623/2.19 |
| 4,042,979 A | 8/1977 | Angell | |
| 4,055,861 A | 11/1977 | Carpentier et al. | |
| 4,164,046 A * | 8/1979 | Cooley | 623/2.36 |
| 4,703,676 A | 11/1987 | Mayer | |
| 4,743,253 A | 5/1988 | Magladry | |
| 4,865,600 A | 9/1989 | Carpentier et al. | |
| 4,932,965 A | 6/1990 | Phillips | |
| 5,061,277 A | 10/1991 | Carpentier et al. | |
| 5,089,015 A | 2/1992 | Ross | |
| 5,104,407 A | 4/1992 | Lam et al. | |
| 5,306,296 A | 4/1994 | Wright et al. | |
| 5,350,420 A | 9/1994 | Cosgrove et al. | |
| 5,403,305 A | 4/1995 | Sauter et al. | |
| 5,415,667 A | 5/1995 | Frater | |
| 5,522,884 A | 6/1996 | Wright | |
| 5,607,471 A | 3/1997 | Seguin et al. | |

(Continued)

FOREIGN PATENT DOCUMENTS

EP   0 338 994   10/1989

(Continued)

OTHER PUBLICATIONS

Alonso-Lej, F., "The 'dynamic' mitral ring: A new concept in treating mitral insufficiency", Recent Progress in Mitral Valve Disease, pp. 45 and 443-449 (1984).

(Continued)

*Primary Examiner* — David Isabella
*Assistant Examiner* — Suba Ganesan
(74) *Attorney, Agent, or Firm* — Lerner, David, Littenberg, Krumholz & Mentlik, LLP

(57) ABSTRACT

An annuloplasty prosthesis for a heart valve has a sewing cuff added to the conventional structure. The sewing cuff is preferably an extension of the fabric cover that is provided around the core of the prosthesis. The sewing cuff preferably extends radially outwardly from cross sections of the remainder of the prosthesis. Methods of making such a sewing cuff are also disclosed.

7 Claims, 5 Drawing Sheets

U.S. PATENT DOCUMENTS

| | | | |
|---|---|---|---|
| 5,669,919 A | 9/1997 | Sanders et al. | |
| 5,755,783 A * | 5/1998 | Stobie et al. | 623/2.39 |
| 5,800,531 A | 9/1998 | Cosgrove et al. | |
| 5,814,097 A | 9/1998 | Sterman et al. | |
| 5,814,101 A | 9/1998 | Wallner et al. | |
| 5,824,066 A | 10/1998 | Gross et al. | |
| 5,843,177 A | 12/1998 | Vanney et al. | |
| 5,888,240 A | 3/1999 | Carpentier et al. | |
| 5,972,030 A | 10/1999 | Garrison et al. | |
| 6,001,127 A | 12/1999 | Schoon et al. | |
| 6,019,739 A | 2/2000 | Rhee et al. | |
| 6,143,024 A | 11/2000 | Campbell et al. | |
| 6,187,040 B1 | 2/2001 | Wright | |
| 6,214,043 B1 | 4/2001 | Krueger et al. | |
| 6,217,610 B1 | 4/2001 | Carpentier et al. | |
| 6,231,602 B1 | 5/2001 | Carpentier et al. | |
| 6,283,993 B1 | 9/2001 | Cosgrove et al. | |
| 6,319,280 B1 | 11/2001 | Schoon | |
| 6,368,348 B1 | 4/2002 | Gabbay | |
| 6,391,054 B2 | 5/2002 | Carpentier et al. | |
| 6,406,492 B1 | 6/2002 | Lytle | |
| 6,409,758 B2 | 6/2002 | Stobie et al. | |
| 6,451,054 B1 | 9/2002 | Stevens | |
| 6,564,805 B2 | 5/2003 | Garrison et al. | |
| 6,602,289 B1 | 8/2003 | Colvin et al. | |
| 6,689,163 B2 | 2/2004 | Lytle | |
| 6,702,852 B2 | 3/2004 | Stobie et al. | |
| 6,719,786 B2 | 4/2004 | Ryan et al. | |
| 6,726,717 B2 | 4/2004 | Alfieri et al. | |
| 6,730,121 B2 | 5/2004 | Ortiz et al. | |
| 6,749,630 B2 | 6/2004 | McCarthy et al. | |
| 6,786,924 B2 | 9/2004 | Ryan et al. | |
| 2002/0129820 A1 | 9/2002 | Ryan et al. | |
| 2002/0133180 A1 | 9/2002 | Ryan et al. | |
| 2002/0173844 A1 | 11/2002 | Alfieri et al. | |
| 2002/0183839 A1 | 12/2002 | Garrison et al. | |
| 2003/0045929 A1 | 3/2003 | McCarthy et al. | |
| 2003/0050693 A1 | 3/2003 | Quijano et al. | |
| 2003/0093148 A1 | 5/2003 | Bolling et al. | |
| 2003/0144732 A1 | 7/2003 | Cosgrove et al. | |
| 2003/0176916 A1 | 9/2003 | Ryan et al. | |
| 2003/0176917 A1 | 9/2003 | Ryan et al. | |
| 2003/0199975 A1 | 10/2003 | Gabbay | |
| 2004/0006384 A1 | 1/2004 | McCarthy | |
| 2004/0019357 A1 | 1/2004 | Campbell et al. | |
| 2004/0034410 A1 | 2/2004 | Holmberg | |
| 2004/0133273 A1 | 7/2004 | Cox | |
| 2004/0186564 A1 | 9/2004 | Ryan et al. | |
| 2004/0249453 A1 | 12/2004 | Cartledge et al. | |

FOREIGN PATENT DOCUMENTS

| | | |
|---|---|---|
| EP | 0 375 181 | 6/1990 |
| EP | 0 495 417 | 7/1992 |
| EP | 0 595 791 | 5/1994 |
| EP | 1 034 753 | 9/2000 |
| WO | WO 91/17721 | 11/1991 |
| WO | WO 99/04730 | 2/1999 |
| WO | WO 02/074197 | 9/2002 |
| WO | WO 03/020178 | 3/2003 |
| WO | WO 03/053289 | 7/2003 |

OTHER PUBLICATIONS

Belcher, J.R., "The Surgical Treatment of Mitral Regurgitation", British Heart Journal vol. 26, pp. 513-523 (1964).

Carpentier, A., "La Valvuloplastie Reconstitutive: Une Nouvelle Technique de Valvuloplastie Mitrale", Technique Chirugicale, No. 7, pp. 251-255 (1969).

Carpentier, A., et al., "A New Reconstructive Operation for Correction of Mitral and Tricuspid Insufficiency", The Journal of Thoracic and Cardiovascular Surgery, vol. 61, No. 1, pp. 1-13 (1971).

Duran, C.G., et al., "Clinical and Hemodynamic Performance of a Totally Flexible Prosthetic Ring for Atrioventricular Valve Reconstruction", The Annals of Thoracic Surgery, vol. 22, No. 5, pp. 458-463 (1976).

Cooley, D.A., et al., "Mitral Leaflet Prolapse: Surgical Treatment using a Posterior Annular Collar Prosthesis", Cardiovascular Diseases Bulletin of the Texas Heart Institute, vol. 3, No. 4, pp. 438-443 (1976).

Duran, C.G., "Reconstructive procedures of the Mitral Valve Including Ring Annuloplasty", Modern Technics in Surgery, 20 (1979).

Eric, M.K., "Morphological and Functional Reconstruction of the Mitral Valve: A New Annuloplastic Procedure," Texas Heart Institute Journal, vol. 9, pp. 329-334 (1982).

Castells, E., et al., "Long-Term Results With the Puig Massana-Shiley Annuloplasty Ring", The Journal of Cardiovascular Surgery, Abstracts, vol. 24 No. 4, p. 387 (1983).

Henze, A., et al., "The Adjustable Half-Moon: An Alternative Device for Tricuspid Valve Annuloplasty", Scandinavian Journal of Thoracic and Cardiovascular Surgery, vol. 18, pp. 29-32 (1984).

Reece, I.J., et al., "Surgical Treatment of Mitral Systolic Click Syndrome: Results in 37 Patients", The Annals of Thoracic Surgery, vol. 39, No. 2, pp. 155-158 (1985).

Morse, D., et al., "Cardiac Valve Identification Atlas and Guide", Chapter 10 in Guide to Prosthetic Cardiac Valves, edited by Dryden Morse, Robert M. Steiner, and Javier Fernandez, Springer-Verlag New York Inc. (1985).

Durán, C.M.G., et al., "A New Absorbable Annuloplasty Ring in the Tricuspid Position: An Experimental Study", The Thoracic and Cardiovascular Surgeon, vol. 34, No. 6, pp. 377-379 (1986).

Levine, R.A., et al., "The Relationship of Mitral Annular Shape to the Diagnosis of Mitral Valve Prolapse", Circulation, vol. 75, No. 4, pp. 756-767 (1987).

Murphy, J. P. et al., "The Puig-Massana-Shiley Annuloplasty Ring for Mitral Valve Repair: Experience in 126 Patients," The Annals of Thoracic Surgery, vol. 43, pp. 52-58 (1987).

Ahmadi, A., et al., "Hemodynamic Changes Following Experimental Production and Correction of Acute Mitral Regurgitation With An Adjustable Ring Prosthesis", The Thoracic and Cardiovascular Surgeon, vol. 36, No. 6, pp. 313-319 (1988).

Duran, C.G., et al., "Stability of Mitral Reconstructive Surgery at 10-12 Years for Predominantly Rheumatic Valvular Disease", Circulation Supplement I, vol. 78, No. 3, pp. I-91-I-96 (1988).

Gregori, F., Jr., et al., "Um Novo Modelo De Anel Protetico Para Pacientes Corn Insuficiencia Valvar Mitral. Relato de Dois Casos", Arquivos Brasileiros de Cardiologia, vol. 50, No. 6, pp. 417-420 (1988).

Shumway, S.J., et al., "A 'Designer' Annuloplasty Ring for Patients with Massive Mitral Annular Dilation", The Annals of Thoracic Surgery, vol. 46, No. 6, pp. 695-696 (1988).

Erk, M.K., et al., "Semi-frame Mitral Annuloplasty", Cardiac Reconstructions pp. 157-163 (1989).

Chachques, J.C., et al., "Absorbable Rings for Pediatric Valvuloplasty: Preliminary Study", Supplement IV to Circulation, vol. 82, No. 5, pp. IV-82-IV-88 (1990).

Deloche, A., et al., "Valve Repair With Carpentier Techniques", The Journal of Thoracic and Cardiovascular Surgery, vol. 99, No. 6, pp. 990-1002 (1990).

Duran, C.M.G., et al., "Valve Repair in Rheumatic Mitral Disease", Supplement to Circulation vol. 84, No. 5, pp. III 125-III 132 (1990).

Fundarò, P., et al., "Polytetrafluoroethylene Posterior Annuloplasty for Mitral Regurgitation", The Annals of Thoracic Surgery, Correspondence, vol. 50, No. 1, pp. 165-166 (1990).

Hendren, W.G., et al., "Mitral Valve Repair for Ischemic Mitral Insufficiency", The Annals of Thoracic Surgery, vol. 52, pp. 1246-1252 (1991).

Salati, M., et al., "Posterior Pericardial Annuloplasty: A Physiological Correction?", European Journal of Cardio-Thoracic Surgery, vol. 5, pp. 226-229 (1991).

Cooley, D.A., "Ischemic Mitral Insufficiency", Cardiac Surgery: State of the Art Reviews, vol. 6, No. 2, pp. 237-249 (1992).

Martin, S. L., et al., "Echocardiographic Evaluation of Anuloplasty Rings: Comparison of Continuity Equation and Pressure Half-Time Methods", Journal of the American Society of Echocardiography, vol. 5, No. 3, p. 322 (1992).

Суdарикоβ, В.Ф, et al., "АННУПОПАСТNКА ТРNКУСПNОАПЬНОГО КПАПАНА РЕГУПNРУЕМЫIМ

ПОПУКОПЬUOM ПОО КОНТРОПЕМ УРЕСПNWEBOOHON EXOKAPOHOГPAΦNN", КОПППЕКТNВ АВТОРОВ (1992).

Cooley, D.A., et al., "A Cost-Effective Dacron Annuloplasty Ring", The Annals of Thoracic Surgery, vol. 56, pp. 185-186 (1993).

Pellegrini, A., et al., "Posterior Annuloplasty in the Surgical Treatment of Mitral Insufficiency", The Journal of Heart Valve Disease, vol. 2, pp. 633-638 (1993).

Salvador, L. et al., "The Pericardium Reinforced Suture Annuloplasty: Another Tool Available for Mitral Annulus Repair," Journal of Cardiac Surgery, vol. 8, pp. 79-84 (1993).

Victor, S. et al., "Truly Flexible D-Shaped Autogenous Pericardial Ring for Mitral Annuloplasty," The Annals of Thoracic Surgery, vol. 56, pp. 179-180 (1993).

Gorton, M.E. et al., "Mitral Valve Repair Using a Flexible and Adjustable Annuloplasty Ring," The Annals of Thoracic Surgery, vol. 55, pp. 860-863 (1993).

Salati, M. et al., "Annular Remodelling With Pericardial Reinforcement: Surgical Technique and Early Results," The Journal of Heart Valve Disease, vol. 2, pp. 639-641 (1993).

Gregori, F., et al., "Mitral Valvuloplasty With a New Prosthetic Ring", Official Journal of the European Association for Cardio-thoracic surgery, vol. 8, No. 4, pp. 168-172 (1994).

Carpentier, A.F., et al., The 'Physio-Ring': An Advanced Concept in Mitral Valve Annuloplasty, Ann. Thorac. Surg. vol. 60, No. 5, pp. 1177-1186 (1995).

Melo, J.Q., et al. "Surgery for Acquired Heart Disease: Atrioventricular Valve Repair Using Externally Adjustable Flexible Rings", The Journal of Thoracic and Cardiovascular Surgery No. 110, pp. 1333-1337 (1995).

Bolling, S.F., et al., "Surgery For Acquired Heart Disease", The Journal of Thoracic and Cardiovascular Surgery, vol. 109, No. 4, pp. 676-683 (1995).

Cosgrove, D.M. III, et al, "Initial Experience With the Cosgrove-Edwards Annuloplasty System", The Annals of Thoracic Surgery, vol. 60, pp. 499-504 (1995).

Katz, N.M., "Current Surgical Treatment of Valvular Heart Disease", American Family Physician, vol. 52, No. 2, pp. 559-568 (1995).

Ghosh, P.K., "Mitral Annuloplasty: A Right-Side View," The Journal of Heart Valve Disease, vol. 5, pp. 286-293 (1996).

Vongpatanasin, W., et al., "Prosthetic Heart Valves", The New England Journal of Medicine, vol. 335, No. 6, pp. 407-416 (1996).

Kasegawa, H., et al., "Physiologic Remodeling Annuloplasty to Retain the Shape of the Anterior Leaflet: A New Concept in Mitral Valve Repair", The Journal of Heart Valve Disease, vol. 6, pp. 604-607 (1997).

Kurosawa, H., et al., "Mitral Valve Repair by Carpentier-Edwards Physio Annuloplasty Ring", The Japanese Journal of Thoracic and Cardiovascular Surgery, vol. 47, pp. 355-360 (1999).

Smolens, I., et al., "Current Status of Mitral Valve Reconstruction in Patients with Dilated Cardiomyopathy", Ital. Heart J., vol. 1, No. 8, pp. 517-520 (2000).

Lachmann, J., MD, et al., "Mitral Ring Annuloplasty: An Incomplete Correction of Functional Mitral Regurgitation Associated with Left Ventricular Remodeling", Current Cardiology Reports, vol. 3, pp. 241-246 (2001).

Rubenstein, F., et al., "Alternatives in Selection of Rings for Mitral Annuloplasty", Current Opinon in Cardiology, vol. 16, No. 2, pp. 136-139 (2001).

Bolling, S.F., "Mitral Reconstruction in Cardiomyopathy", The Journal of Heart Valve Disease, vol. 11, Suppl. 1, pp. S26-S31 (2002).

Ogus, T.N., et al., "Posterior Mitral Annuloplasty with an Adjustable Homemade Ring", Journal of Cardiac Surgery, vol. 17, No. 3, pp. 226-228 (2002).

Kaye, D.M., et al., "Feasibility and Short-Term Efficacy of Percutaneous Mitral Annular Reduction for the Therapy of Heart Failure—Induced Mitral Regurgitation, Circulation, Brief Rapid Communication", No. 108, pp. 1795-1797 (2003).

* cited by examiner

HEART VALVE ANNULOPLASTY PROSTHESIS SEWING CUFFS AND METHODS OF MAKING SAME

This application claims the benefit of U.S. provisional patent application No. 60/571,437, filed May 14, 2004, which is hereby incorporated by reference herein in its entirety.

BACKGROUND OF THE INVENTION

Annuloplasty prostheses for heart valves are well known as is shown, for example, by Alfieri et al. U.S. patent application publication US 2002/0173844 A1 and Bolling et al. U.S. patent application publication US 2003/0093148 A1. Such prostheses may be complete rings (e.g., as in the above-mentioned Alfieri et al. and Bolling et al. references), or they may be less than complete rings (e.g., as in Carpentier U.S. Pat. No. 3,656,185). The term "annuloplasty" is used herein to refer to both of these types of prostheses (i.e., both complete rings and less than completely annular structures (e.g., generally C-shaped structures)).

Typical annuloplasty prostheses include a core member surrounded by a soft fabric cover. The core member is often substantially rigid or at least semi-rigid and not penetrable by a suture needle and suture material. The fabric cover may be designed to cushion the prosthesis, and possibly also to promote tissue in-growth into the prosthesis to help integrate the prosthesis into the patient's body. It is often desired to secure the prosthesis in the patient by passing one or more suture needles and suture material through the fabric cover and adjacent tissue. Tightness and/or thinness of the fabric cover may make this difficult to do. Even if the surgeon is successful in getting proper engagement, the amount of fabric caught may be less than would be desirable for good tissue healing and over-growth.

SUMMARY OF THE INVENTION

To facilitate suturing an annuloplasty prosthesis into a patient, a sewing cuff is added to the prosthesis in accordance with the invention. Such a sewing cuff is preferably an extension of the fabric cover that is provided around the core of the prosthesis. The sewing cuff preferably extends radially outwardly from cross sections of the core and the remainder of the fabric cover. Stitching may be used to stabilize the extension. The extension may be one-piece with the fabric cover. For example, a medial portion of the cover fabric may be used to form the extension. As another example, a free edge portion of the fabric used for the cover may be used to provide the extension. The free edge portion may be folded to increase the bulk of the extension. Two free edge portions of the fabric used for the cover may be used together to form the extension. Again, folding may be used to increase the bulk of the extension.

The invention also includes various methods of making sewing cuffs such as those summarized in the preceding paragraph.

Further features of the invention, its nature and various advantages, will be more apparent from the accompanying drawings and the following detailed description of the preferred embodiments.

BRIEF DESCRIPTION OF THE DRAWINGS

FIG. 1 may be taken as shown at 1-1 in FIG. 7.

DETAILED DESCRIPTION

Figure 1:
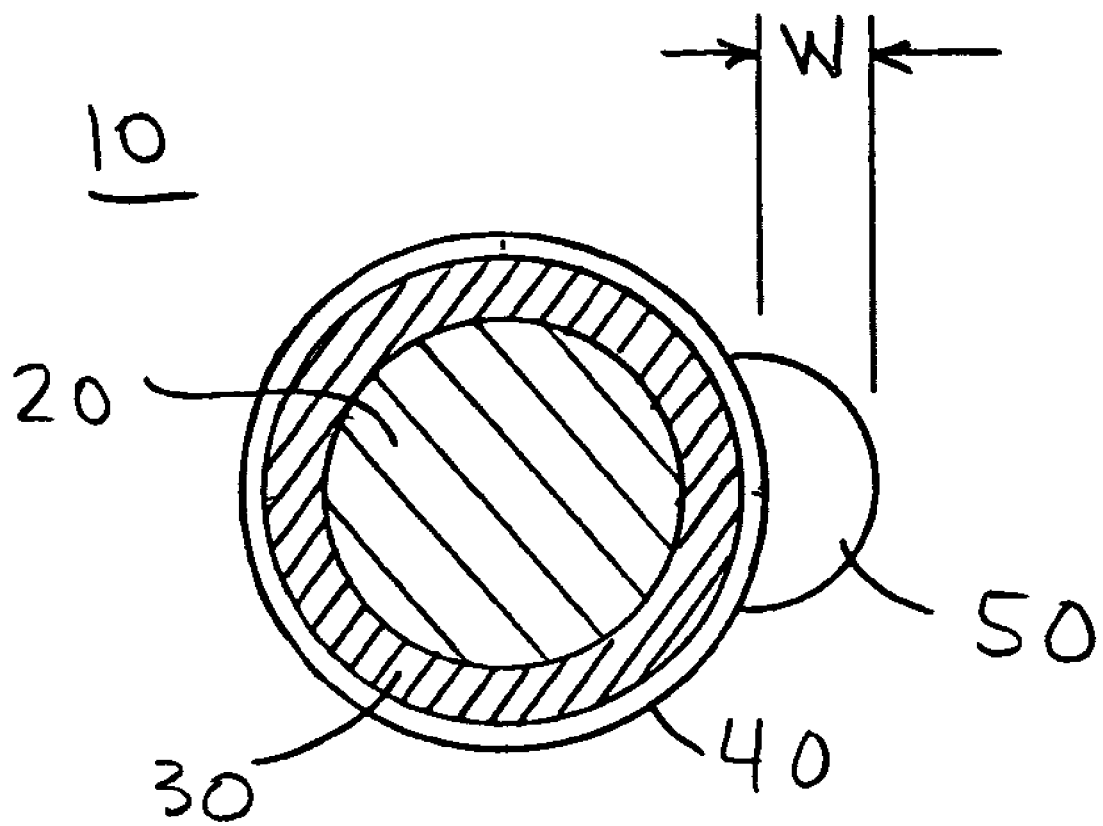
FIG. 1 is a simplified cross sectional view of an illustrative embodiment of an annuloplasty prosthesis for a heart valve in accordance with the invention.
Figure 7:
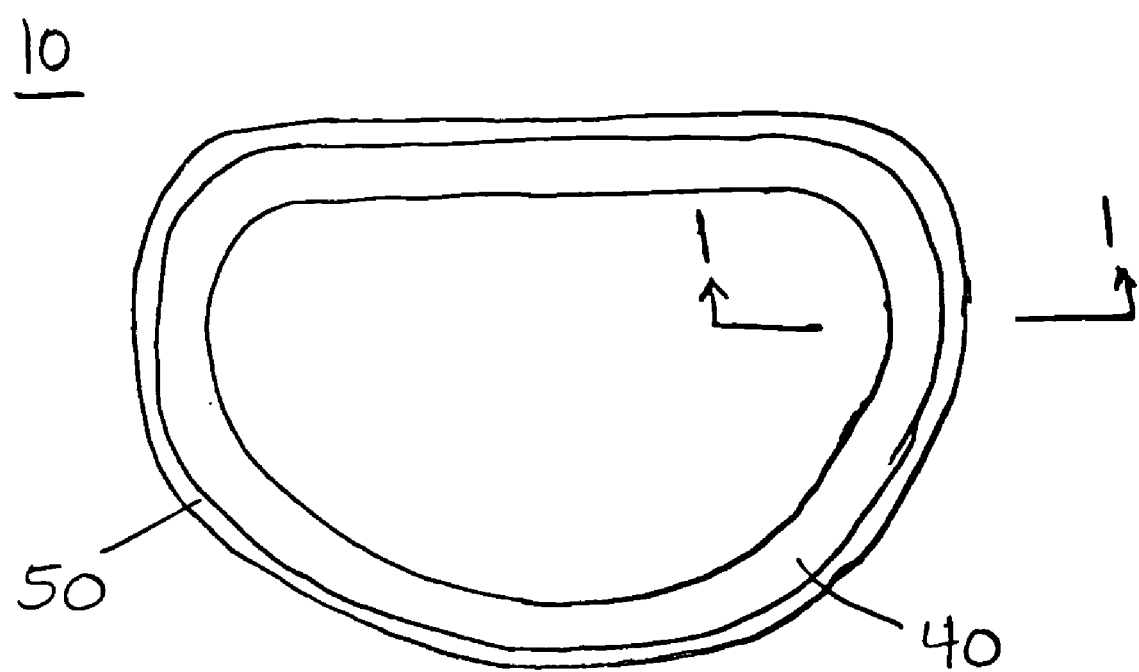
FIG. 7 is a simplified plan view of an illustrative embodiment of a prosthesis in accordance with the invention.

The annuloplasty prosthesis 10 cross section shown in FIG. 1 includes core member 20, a layer 30 of an elastomeric material surrounding core 20, and fabric cover 40 surrounding elements 20 and 30. FIG. 1 also shows what may be described as a mini-sewing-cuff 50 extending radially outwardly from the other elements at one angular location or region around the circumference of the cross section. For completeness FIG. 7 shows a plan view of an entire illustrative annuloplasty prosthesis 10 in accordance with the invention and which can have a cross section as shown in FIG. 1 (or as in other FIGS. subsequent to FIG. 1). Although FIG. 7 shows the cross section taken at one particular location, substantially the same cross section may be found at other (or even all) locations annularly around prosthesis 10. Also, although FIG. 7 shows a prosthesis 10 that is a complete, unbroken, generally D-shaped annulus, prosthesis 10 could have other shapes, and could alternatively be only a portion of an annulus (e.g., it could be C-shaped rather than D-shaped). Still another point to be made is that although FIG. 7 shows sewing cuff 50 extending around the outside of prosthesis 10, sewing cuff 50 could alternatively be at any other location around cross sections of the prosthesis.

FIG. 7 is provided to make the point that, although most of the other FIGS. herein are of cross sections, these other FIGS. are representative cross sections of structures that extend longitudinally (e.g., out of the plane of the paper on which the cross sections are drawn).

Typical materials for the various components of prosthesis 10 will be mentioned later in this specification. For the moment it will be sufficient to point out that elastomeric layer 30 is optional and may be omitted in some embodiments of the invention. Fabric cover 40 would then be directly over core 20. The FIGS. subsequent to FIG. 1 show generalized cores 20, which can be either like core 20 in FIG. 1 or a composite of elements such as 20 and 30 in FIG. 1.

Sewing cuff 50 can be formed on prosthesis 10 in any of a number of different ways. Some examples are shown in subsequent FIGS. and described below.

Figure 2A:
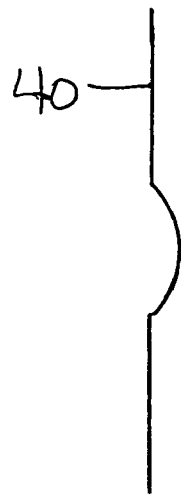
FIG. 2a is a simplified cross sectional view of an illustrative embodiment of a component that can be used in making a prosthesis like that shown in FIG. 1 in accordance with the invention.
Figure 2B:
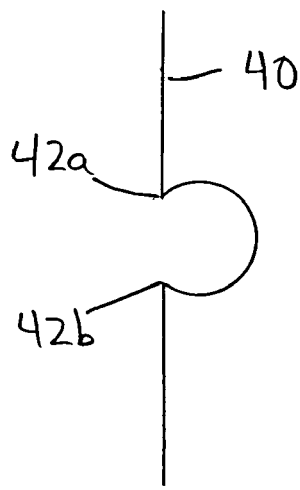
FIG. 2b is similar to FIG. 2a, but shows a later stage in handling the component in accordance with the invention.
Figure 2C:
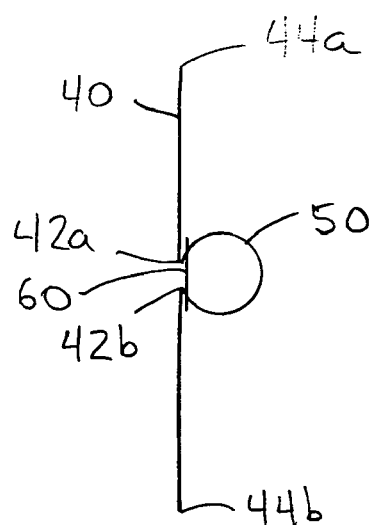
FIG. 2c is again similar to FIGS. 2a and 2b, but shows a still later stage in accordance with the invention.
Figure 2D:
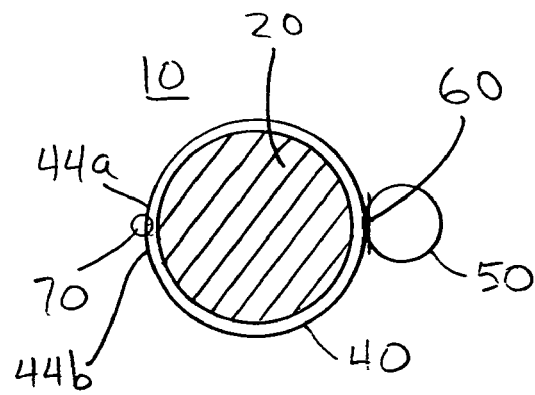
FIG. 2d is generally similar to FIG. 1, but shows an end result from the progression of FIGS. 2a-2c in accordance with the invention.

In the illustrative embodiment shown in FIGS. 2a-2d, a medial (or more generally an interior) portion of fabric 40 is gradually pinched together as shown progressively in FIGS. 2a-2c until two interior creases 42a and 42b are formed and brought together (FIG. 2c). A fine suture 60 is then used to sew the two creases 42 together to create sewing cuff 50. After the sewing cuff has been sewn together, the two free ends (edges) 44a and 44b of fabric 40 are wrapped around prosthesis core 20 and stitched together as shown at 70 in FIG. 2d. Fabric 40 is pulled tightly together during stitching 70 so that it will securely and firmly wrap around prosthesis core 20.

Figure 3A:
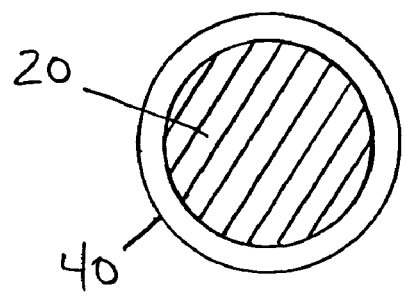
FIGS. 3a-3c are each generally similar to FIG. 1, but show a progression in an alternative approach to making a prosthesis in accordance with the invention.
Figure 3B:
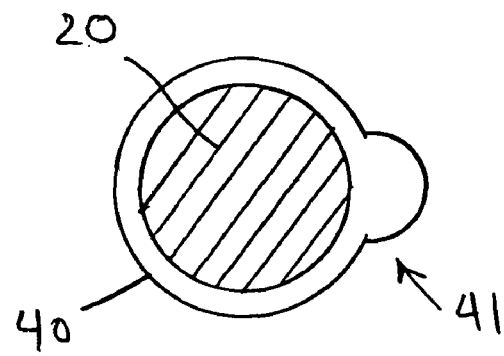
Figure 3C:
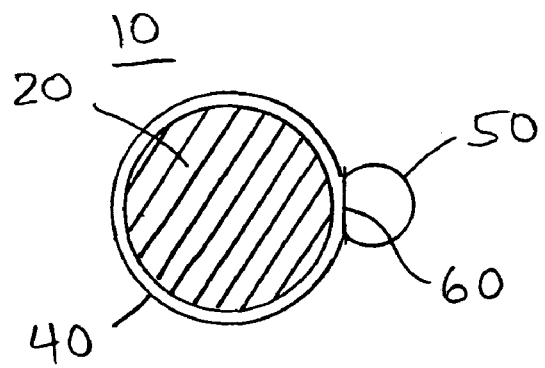

In the alternative embodiment illustrated by FIGS. 3a-3c, fabric cover 40 is first wrapped loosely around prosthesis core 20. A portion of the fabric annulus is gradually squeezed or pinched together as shown at 41 in FIG. 3b. This eventually produces a sewing cuff. Depending on the width of the cuff required, the amount of fabric 40 squeezed or pinched together to create the cuff can vary. Suture 60 is added to hold sewing cuff 50 together as shown in FIG. 3c to complete the process.

Figure 4:
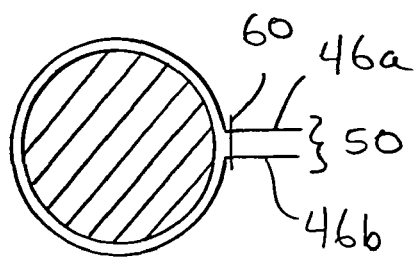
FIG. 4 is again generally similar to FIG. 1, but shows an alternative construction of a prosthesis in accordance with the invention.

In the further alternative embodiment shown in FIG. 4, sewing cuff 50 is created by squeezing together two otherwise free edges 46a and 46b of fabric 40 after the fabric has been wrapped around prosthesis core 20. A fine suture 60 can then be used to stitch the two single-layers fabric edges together (and around core 20) to form the sewing cuff. The width (radial outward projection) of the cuff (dimension W in FIG. 1) can be determined by adjusting the amount of excess fabric 40 used to wrap around the core. More than just the single stitch line 60 can be used to hold edges 46a and 46b together in sewing cuff 50.

Figure 5:
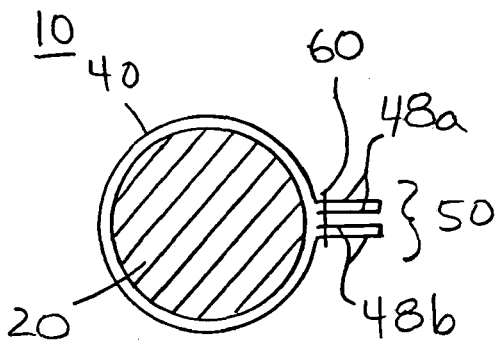
FIG. 5 is once again generally similar to FIG. 1, but shows another alternative construction of a prosthesis in accordance with the invention.

In the still further alternative embodiment shown in FIG. 5, fabric 40 is loosely wrapped around prosthesis core 20 with both edges 48a and 48b free. Free edges 48 are then folded over on themselves so that each free edge becomes double-layered. The two double-layered free edges are then squeezed together, and a fine suture 60 is used to stitch the fabric together to form sewing cuff 50. A sewing cuff created in this way can be thicker (bulkier) and provide more cushioning. Free edges 48 can also be folded over multiple times to create a triple- or other multiple-layered cuff 50.

Figure 6:
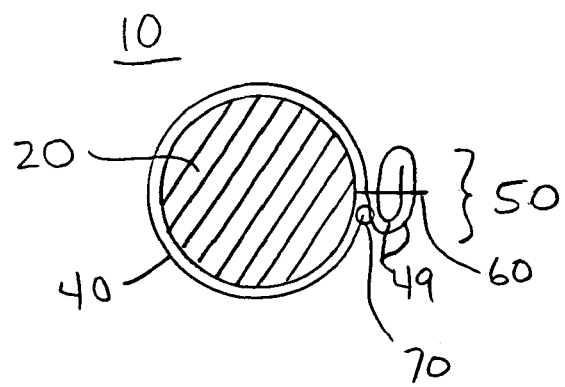
FIG. 6 is again generally similar to FIG. 1, but shows still another alternative construction of a prosthesis in accordance with the invention.

In the further illustrative embodiment shown in FIG. 6, sewing cuff 50 is first formed by folding a free edge portion of fabric 40 several times as shown at 49 to get the thickness desired. This is then stitched together with suture 60 so that the sewing cuff is stabilized and remains intact with the desired shape. The remaining free edge of fabric 40 is used to wrap around prosthesis core 20 and then stitched to the sewing cuff as shown at 70. Fabric 40 will wrap around ring core 20 securely and firmly when the process is completed.

Sewing cuff 50 may measure from about 0.25 mm to about 5.0 mm in width (see dimension W in FIG. 1 or the comparable unreferenced dimension in any of the other FIGS.). The sewing cuff may be created from a soft fabric such as polyester, PTFE, or the like, and may be the same as (or even one piece with) fabric cover 40. Sewing cuff 50 allows the surgeon to place sutures easily, and also provides substantially more fabric for tissue in-growth purposes. More sewing fabric also allows for a better cushion between the heart valve annulus and the prosthesis. As has been said, sewing cuff 50 can also be used with a prosthesis core that is first covered by a soft elastomer 30, such as silicone or the like, before it is covered by a fabric 40 with cuff 50. The sewing cuff can also be used on just prosthesis core 20 itself without any intermediate elastomer covering 30. Prosthesis core 20 can be made from any suitable material, such as stainless steel, titanium, ceramic, elgiloy, shape-memory alloy, and/or polymeric material.

It will be understood that the foregoing is only illustrative of the principles of the invention, and that various modifications can be made by those skilled in the art without departing from the scope and spirit of the invention. For example, although the FIGS. herein show prostheses having cores 20 that are round in cross section, it will be appreciated that other core cross sectional shapes can be used instead if desired.

The invention claimed is:

1. A method of making an annuloplasty prosthesis for a heart valve comprising:
   providing a piece of fabric having free edges that are substantially parallel to one another on respective opposite sides of a width of the fabric;
   creasing the fabric along each of two crease lines that are each substantially parallel to the free edges and that are spaced from one another and the free edges widthwise of the fabric;
   bringing the two crease lines into lengthwise contact with one another without enclosing portions of the width of the fabric that are not between the crease lines;
   stitching the crease lines together along their length to produce a sewing cuff from the portion of the width of the fabric that is between the crease lines;
   providing an annuloplasty prosthesis core annulus;
   after the step of stitching the crease lines together, wrapping the portions of the width of the fabric that are not between the crease lines tightly around the core annulus while positioning the fabric so that the sewing cuff forms an annulus that parallels the core annulus, so that the fabric is securely and firmly wrapped around the core annulus, and so that the free edges come together lengthwise along a line that is spaced from the crease lines; and
   stitching the free edges together lengthwise.

2. The method defined in claim 1, wherein the wrapping step includes positioning the fabric so that the sewing cuff extends radially outwardly from the core annulus.

3. The method defined in claim 2, wherein the wrapping step includes positioning the fabric so that the free edges come together along a line that is opposite from the sewing cuff across cross sections of the core annulus.

4. The method defined in claim 1, wherein the step of providing an annuloplasty prosthesis core annulus comprises:
   providing a core member that is covered by an elastomeric material.

5. The method defined in claim 4, wherein the step of providing a core member comprises:
   forming the core member from a material selected from the group consisting of stainless steel, titanium, ceramic, elgiloy, shape-memory alloy, and polymeric material.

6. The method defined in claim 4 wherein the elastomeric material comprises silicone.

7. The method defined in claim 1, wherein the step of providing a piece of fabric comprises:
   selecting the fabric from the group consisting of polyester and PTFE.

* * * * *